United States Patent
Matsui et al.

(10) Patent No.: US 12,264,352 B2
(45) Date of Patent: Apr. 1, 2025

(54) METHOD FOR ENHANCING EXTRACELLULAR VESICLE PRODUCTION

(71) Applicants: Research Foundation of the City University of New York, New York, NY (US); Japanese Foundation for Cancer Research, Tokyo (JP)

(72) Inventors: Hiroshi Matsui, Glen Rock, NJ (US); Kiyotaka Shiba, Tokyo (JP); Min A. Kang, Flushing, NY (US)

(73) Assignees: Research Foundation of the City University of New York, New York, NY (US); Japanese Foundation for Cancer Research, Tokyo (JP)

( * ) Notice: Subject to any disclaimer, the term of this patent is extended or adjusted under 35 U.S.C. 154(b) by 874 days.

(21) Appl. No.: 17/366,950

(22) Filed: Jul. 2, 2021

(65) Prior Publication Data
US 2021/0332401 A1   Oct. 28, 2021

Related U.S. Application Data

(63) Continuation-in-part of application No. 16/436,331, filed on Jun. 10, 2019, now abandoned, which is a continuation-in-part of application No. 15/430,821, filed on Feb. 13, 2017, now abandoned.

(60) Provisional application No. 62/293,852, filed on Feb. 11, 2016.

(51) Int. Cl.
*C12P 21/00*   (2006.01)
*C12N 5/00*    (2006.01)

(52) U.S. Cl.
CPC .......... *C12P 21/00* (2013.01); *C12N 5/0006* (2013.01)

(58) Field of Classification Search
None
See application file for complete search history.

(56) References Cited

U.S. PATENT DOCUMENTS

| | | |
|---|---|---|
| 6,812,023 B1 | 11/2004 | Lamparski et al. |
| 8,658,600 B2 | 2/2014 | Gao et al. |
| 8,758,991 B2 | 6/2014 | Klein et al. |
| 8,901,284 B2 | 12/2014 | Vlassov et al. |
| 2012/0077263 A1 | 3/2012 | Ward et al. |
| 2015/0306232 A1 | 10/2015 | Xu et al. |

OTHER PUBLICATIONS

Gao et al. (Nat Commun. 2012; 3: 1033). (Year: 2012).*
Gao, Y. et al.; Imaging enzyme-triggered self-assembly of small molecules inside live cells; Nature Communications; Feb. 28, 2012; pp. 1-8; 3:1033 | DOI: 10.1038/ncomms2040; MacMillan.
Zhou, J. et al.; Taurine Boosts Cellular Uptake of Small D-Peptides for Enzyme-Instructed Intracellular Molecular Self-Assembly; JACS; Aug. 1, 2015; pp. 10040-10043; vol. 137; J. Am. Chem. Soc.
De Jong, O. et al.; Cellular stress conditions are reflected in the protein and RNA content of endothelial cell-derived exosomes; Journal of Extracellular Vesicles; Apr. 16, 2012; pp. 1-11; Coaction Publishing.
Hedlund, M. et al.; Thermal- and Oxidative Stress Causes Enhanced Release of NKG2D Ligand-Bearing Immunosuppressive Exosomes in Leukemia/Lymphoma T and B Cells; Plos ONE; Feb. 25, 2011; pp. 1-10; vol. 6 | Issue 2; Plos ONE.
Clayton, A. et al.; Induction of heat shock proteins in B-cell exosomes; Journal of Cell Science; Aug. 15, 2005; pp. 3631-3638; 118(Pt 16); the Company of Biologists.
Yu, X. et al.; The Regulation of Exosome Secretion: a Novel Function of the p53 Protein; Cancer Research; May 1, 2006; pp. 4795-4801; vol. 66, Issue 9.
Jamalzadeh, L. et al.; Effects of Some Common Organic Solvents on MCF-7, RAW-264.7 and Human Umbilical Vein Endothelial Cells; Avicenna J Med Biochem; Apr. 30, 2016; 6 pgs; 4(1):e33453.
Amedzadeh, Z. et al.; Assessment of Different Permeabilization Methods of Minimizing Damage to the Adherent Cells for Detection of Intracellular RNA by Flow Cytometry; Avicenna J Med Biochem; Jan. 2014; pp. 38-46vol. 6, Issue 1.
Zhou, J. et al.; Enzyme-Instructed Self-Assembly of Small D-Peptides as a Multiple-Step Process for Selectively Killing Cancer Cells; JACS; Mar. 11, 2016; pp. 3813-3823; vol. 138; DOI: 10.1021/jacs.5b13541.
Koley, D. et al.; Triton X-100 concetration effects on membrane permeability of a single HeLa cell by scanning electrochemical microscopy (SECM); PNAS; Sep. 28, 2010; pp. 16783-16787; vol. 107, No. 39.

* cited by examiner

*Primary Examiner* — Sergio Coffa
(74) *Attorney, Agent, or Firm* — Peter J. Mikesell; Schmeiser, Olsen & Watts, LLP

(57) ABSTRACT

A method for enhancing extracellular vesicle production is described. A peptide that induces polymer formation is incubated with a cell culture which results in enhanced EV production. The peptide penetrates the cells and subsequently polymerizes upon exposure to enzymes (e.g. phosphatase) within the cell. The cells that contain the newly formed polymers have an increased production of EVs. These EVs can be harvested using centrifugation techniques.

9 Claims, 12 Drawing Sheets

Specification includes a Sequence Listing.

NapFFK(NBD)Yp

TIRF image of FL-peptide polymer containing extracellular vesicles

METHOD FOR ENHANCING EXTRACELLULAR VESICLE PRODUCTION

CROSS-REFERENCE TO RELATED APPLICATIONS

This application claims priority to and is a continuation-in-part of U.S. patent application Ser. No. 16/436,331 (filed Jun. 10, 2019) which is a continuation-in-part of U.S. patent application Ser. No. 15/430,821 (filed Feb. 13, 2017) which is a non-provisional of U.S. Patent Application 62/293,852 (filed Feb. 11, 2016), the entirety of which are incorporated herein by reference.

STATEMENT OF FEDERALLY SPONSORED RESEARCH OR DEVELOPMENT

This invention was made with government support under grant number MD007599 awarded by the National Institute of Health. The government has certain rights in the invention.

REFERENCE TO A SEQUENCE LISTING

This application refers to a "Sequence Listing" listed below, which is filed herewith as an electronic document. This electronic document is incorporated herein by reference in its entirety.

BACKGROUND OF THE INVENTION

Bioactive, extracellular vesicles (EVs) (for example exosomes and membrane-shedding vesicles) can bud out from cells and carry functional proteins, RNAs/DNAs, actin fibers, and membranes. Recent studies revealed that these nanoparticles are actually specialized in long-distance intercellular communications between cell types, facilitating transfer of proteins, messenger RNAs (mRNAs), microRNAs, and DNAs from exosomes to recipient cells with high specificity, and transferring these genetic components to recipient cells. This genetic delivery between healthy cells could regulate cellular activities, however in some case it leads to the progression of nervous diseases, toxins, and cancers. For example, EVs released from neuron facilitate diverse functions including removal of harmful stress proteins and amyloid fibril formation, the therapeutic approaches have been proposed to control EV generation for Parkinson's disease and Alzheimer's disease. For cardiovascular activity, EVs from cardiomyocytes (CMs) communicate with endotheilial cells (ECs) to generate neovasculature. The intercellular spreading of HIV and infectious prion were also found to be accelerated by EVs. Recent reports shows that most types of cancer cells shed large numbers of exosomes that carry molecular information about the parent tumor, and cancer-derived EVs could be incorporated in with recipient cells thus influencing tumor progression.

Some EVs, for example derived from engineered immunotherapeutic cells (e.g., engineered T cells) and regenerative therapeutic cells (e.g., stem cells), are expected to be applied as "off-the-shelf" therapeutics because these EVs that carry the same therapeutic proteins and genes from the parental cells are safer (i.e., EVs are not viable) and incur less manufacturing and storage costs. Cancer cell-derived exosomes and microvesicles originated in the brain of glioma-bearing mice, and in patients with glioblastoma multiforme were detected in the brain indicating their ability to cross the blood-brain barrier (BBB). Exosomes derived from bacterial pathogens have been used for a long time for immunogenic vaccines against respective organisms even before the existence of EVs was clear. Therefore, the production of EVs is important for practical medical applications of EVs in broad medical areas, however the bottleneck of this approach is to mass-produce EVs from parental cells.

While EVs could be new therapeutic agents for future medicine as described above, the methodology for enhanced generation of EVs is not currently available. Typically, differential ultracentrifugation, not available in routine hospital laboratories, is used for rapid isolation and analysis of EVs. However, this approach is still time consuming (4-5 hours), and the yield is too low (5-25% recovery) for most downstream analysis and therapeutics. Improved methods for EV production would therefore be desirable.

The discussion above is merely provided for general background information and is not intended to be used as an aid in determining the scope of the claimed subject matter.

BRIEF DESCRIPTION OF THE INVENTION

In a first embodiment, a method of enhanced extracellular vesicle production is provided. The method comprising sequential steps of: treating the plurality of cells with NapFFK(NDB)Yp at a concentration of at least 5 µM and less than 50 µM, wherein the NapFFK(NDB)Yp had been purified to a purity of at least 93%; permitting, for under 30 minutes, the NapFFK(NDB)Yp to polymerize within cells in the plurality of cells due to an enzyme within the cells to form a modified cell culture; and isolating a first quantity of extracellular vesicles from the modified cell culture, wherein the first quantity of extracellular vesicles is greater than a second quantity of extracellular vesicles isolated from a corresponding plurality of cells that was not treated with the NapFFK(NDB)Yp.

In a second embodiment, a method of enhanced extracellular vesicle production is provided. The method comprising sequential steps of: treating the plurality of cells with NapFFK(NDB)Yp at a concentration of at least 5 µM and less than 50 µM, wherein the NapFFK(NDB)Yp had been purified to a purity of at least 93%; permitting, for between 20 minutes and 60 minutes, the NapFFK(NDB)Yp to polymerize within cells in the plurality of cells due to a phosphatase enzyme within the cells to form a modified cell culture; and isolating a first quantity of extracellular vesicles from the modified cell culture, wherein the first quantity of extracellular vesicles is greater than a second quantity of extracellular vesicles isolated from a corresponding plurality of cells that was not treated with the NapFFK(NDB)Yp; wherein the step of isolating occurs between 20 minutes and 60 minutes of the step of treating.

This brief description of the invention is intended only to provide a brief overview of subject matter disclosed herein according to one or more illustrative embodiments and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

In FIG. 6A the peptide in lower purity (75.6%) was used while in FIG. 6B the peptide that was highly purified (99.9%) was applied to cells.

DETAILED DESCRIPTION OF THE INVENTION

This disclosure provides a method for enhancing extracellular vesicle (EV) production. Specifically, a peptide that induces polymer formation is incubated with a cell culture which results in enhanced EV production. The peptide penetrates the cells and subsequently polymerizes upon exposure to enzymes (e.g. phosphatase) within the cell. The cells that contain the newly formed polymers have an increased production of EVs. These EVs can be harvested using centrifugation techniques.

Without wishing to be bound to any particular theory, peptides that are assembled in cells are believed to stress those cells. The stressed cells increase the production of EVs. Because the polymerization of peptides is triggered by enzymes in the cells, there are many peptides that can be polymerized in cells and are therefore useful in the disclosed method. Peptides that polymerize around actin fibers of the cytoskeleton may be particularly effective as this is the location where signals for EV generation and believe to be transferred.

In one embodiment, the method uses the a polypeptide precursor (NapFFK(NDB)Yp). This peptide forms polymers within cells when exposed to enzyme family of phosphatase within the cell. A tripeptide, naphthalene-D-Phe-D-Phe-D-Tyr (also known as naphthalene-FFT) can be also polymerized by phosphatase and used as a polypeptide precursor. Likewise, and in another embodiment, a peptide FFFFCGLDD (SEQ ID NO: 1) forms polymers in cells as it is exposed with enzyme metalloproteinases. In other embodiments, a polypeptide precursor $(NDB)C_{10}H_7CH_2C(O)$—FF—$NHCH_2CH_2OCOCH_2CH_2COOH$ forms polymers in cells as it is exposed with enzyme esterase. A peptide N-palmitoyl-GGGHGPLGLARK-CONH$_2$ (SEQ ID NO: 2) forms polymers in cells as it is exposed with enzyme metalloproteinease. A peptide FEFK (SEQ ID NO: 3) can be polymerized in cells when those cells have enzyme protease. In another embodiment, polymers are produced inside cells by polymerizing two peptides by enzymes. For example, peptides, Fmoc-F and FF, can be polymerized in cells when those cells possess enzyme protease.

Figure 1A:
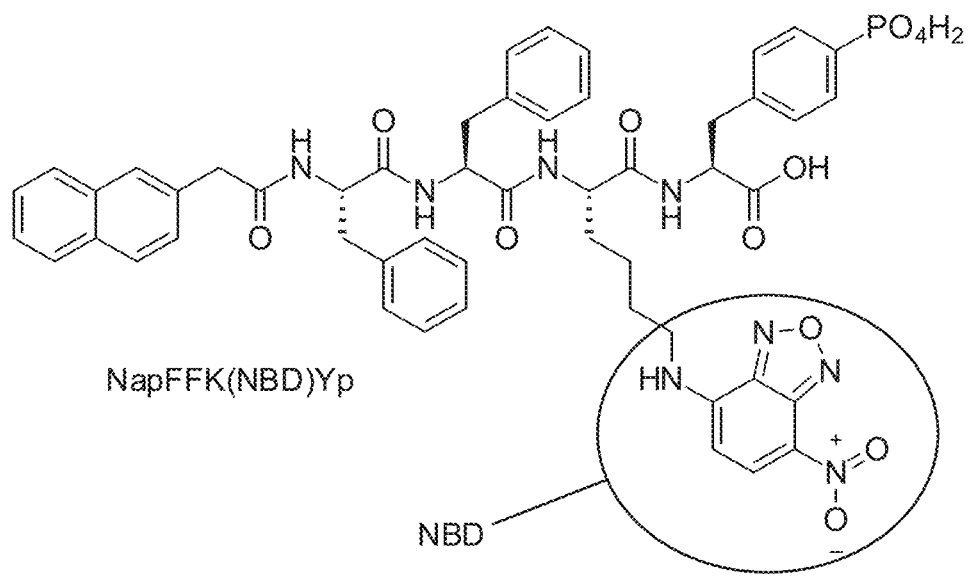
FIG. 1A depicts the chemical structure of NapFFK(NBD)Yp.
Figure 1B:
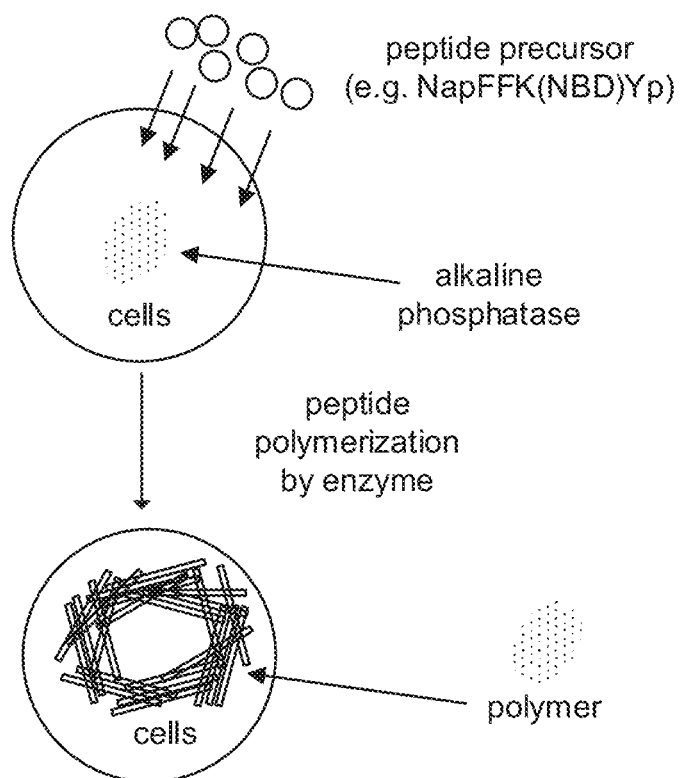
FIG. 1B shows polymers grown inside a cell as an enzyme catalyzes polymerization.

FIG. 1A shows the chemical structure of a peptide polymer precursor, NapFFK(NBD)Yp. NBD (4-nitro-2,1,3-benzoxadiazole) is a fluorophore known to give more intense fluorescence as higher degree of self-assembly. FIG. 1B depicts a scheme to polymerize NapFFK(NBD)Yp with an enzyme inside the cells.

Figure 2A:
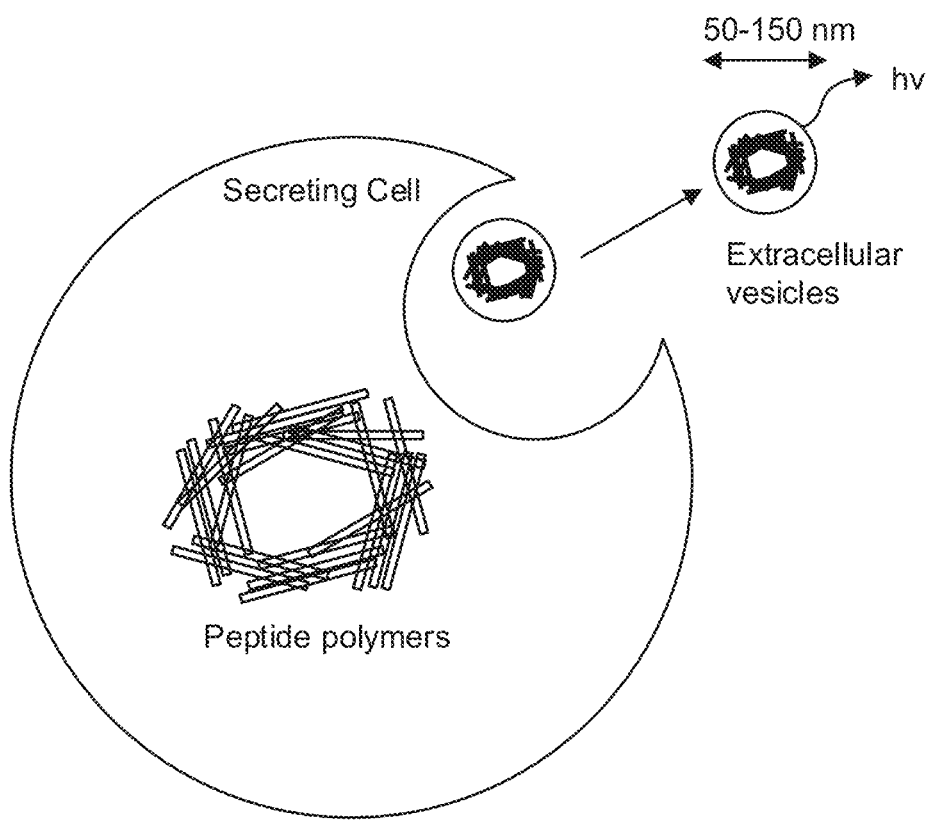
FIG. 2A depicts extracellular vesicles (EVs) release from cells.
Figure 2B:
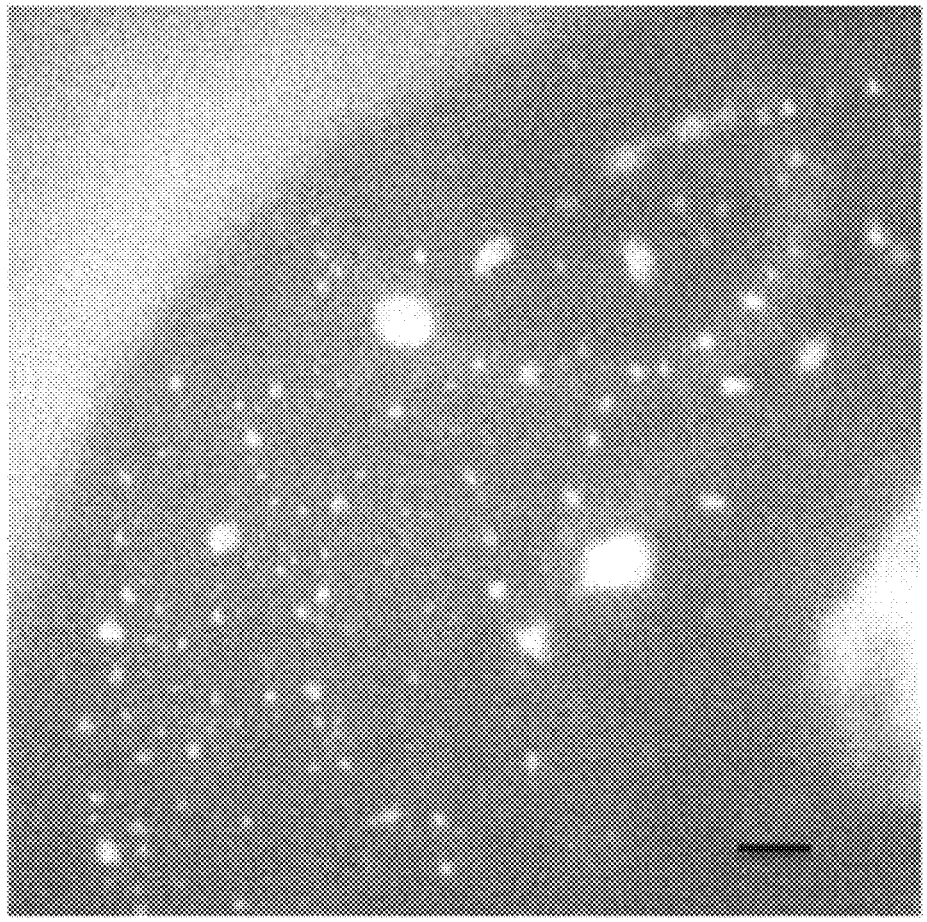
FIG. 2B illustrates TIRF image of EVs secreted from breast cancer cells that incorporate the polypeptide before the EV release.

FIG. 2A depicts extracellular vesicles (EVs) release from cells, multivesicular bodies (MVBs) created in endosomes fuse to the cell surface and release the vesicular content as EVs. EVs of shedding microvesicles could also bud directly from the cell surface. FIG. 2B illustrates TIRF image of 80 nm EVs secreted from MB231 breast cancer cells that incorporate the polypeptide before the EV release. The scale bar=300 nm. In FIG. 2B EVs were extracted from parental MB231 cells containing peptide polymers. In this image, only nanoparticles carrying fluorescent molecules are visible and thus the appearance of bright nanoparticle images indicates that the peptide is successfully polymerized in these cells and these polymers are carried over to EVs through the secretion process and also carry the peptide polymers in Total Internal Reflection Fluorescence (TIRF) microscopy.

Examples of enzymes that promote the polymerization of peptides within cells include phosphatase enzymes, tyrosine phosphatase, esterase, proteinease, protease, metalloproteinease, thermolysine (e.g. polymerization of D-diphenylalanine).

When a peptide precursor of NapFFK(NBD)Yp (FIG. 1A) is added to cells, polymers are grown inside as the enzyme alkaline phosphatases (ALP) in cells catalyze polymerization via dephosphorylation of precursor (FIG. 1B). This precursor contains a fluorophore of NBD (4-nitro-2,1,3-benzoxadiazole, emission wavelength: 510-650 nm), known to give more intense fluorescence with higher degree of self-assembly. To incorporate the peptide in cells, 2.0 ml of 50 μM NapFFK(NBD)Yp is incubated with cells into T-75 flasks and these flasks are kept in an incubator. After 1 hour, this peptide enters cells and ALP around the cytoskeleton polymerizes the peptide. If the microscopic observation of cells undergoing peptide polymerization inside suggests high stress for certain cell types, the peptide incubation with cells is split over 3 days as one-third of total peptide concentration is injected each day. In one embodiment, the peptide was taken by cells without the use of membrane-penetrating agents. These peptides are polymerized around cytoskeleton in MB231 breast cancer cells (where actin fibers and peptide polymers overlap) in fluorescence microscopy. It should be noted that other families of phosphatase enzymes, such as tyrosine phosphatase, can also accomplish this protocol by dephosphorylating the peptide.

In one embodiment, the polymer-incorporated EV extraction from cells is performed in the following order. (1) Centrifuge the conditioned media at 500 g for 10 minutes at 10° C. to form a pellet of cells (2) Centrifuge the conditioned media in 1 at 3000 g for 10 minutes at 10° C. to form another pellet of cells (3) Ultracentrifuge the supernatant of 1 and 2 at 12,000 g for 20 minutes at 10° C. to form a pellet debris (4) Ultracentrifuge the supernatant fraction of 3 at 100,000 g for 70 minutes at 10° C. EVs are contained in a pellet (5) Re-suspend the pellet in 4 in 15.0 ml PBS buffer in the tube, and ultracentrifuge again at 100.000×g for 70 minutes at 10° C. (6) Remove the supernatant fraction of 5. These EVs are collected in this pellet (7) Turn the tube down on a paper towel to remove the excess amount of PBS buffer and let dry the content remained in the tube (8) Re-suspend the pellet in the tube in 100 μL of PBS buffer (9) Store the sample at −20° C.

Figure 3A:
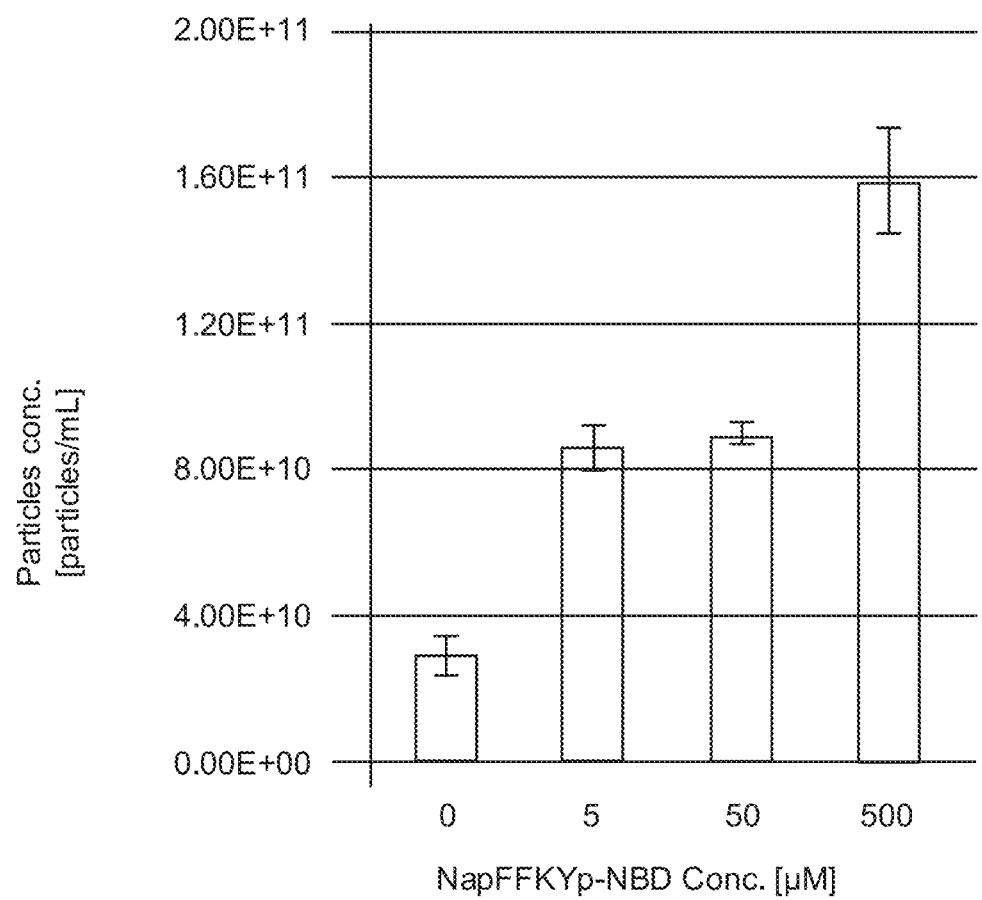
FIG. 3A is a graph showing the number of exosomes released from MDA-MB231 breast cancer cells as a function of polypeptide precursor.
Figure 3B:
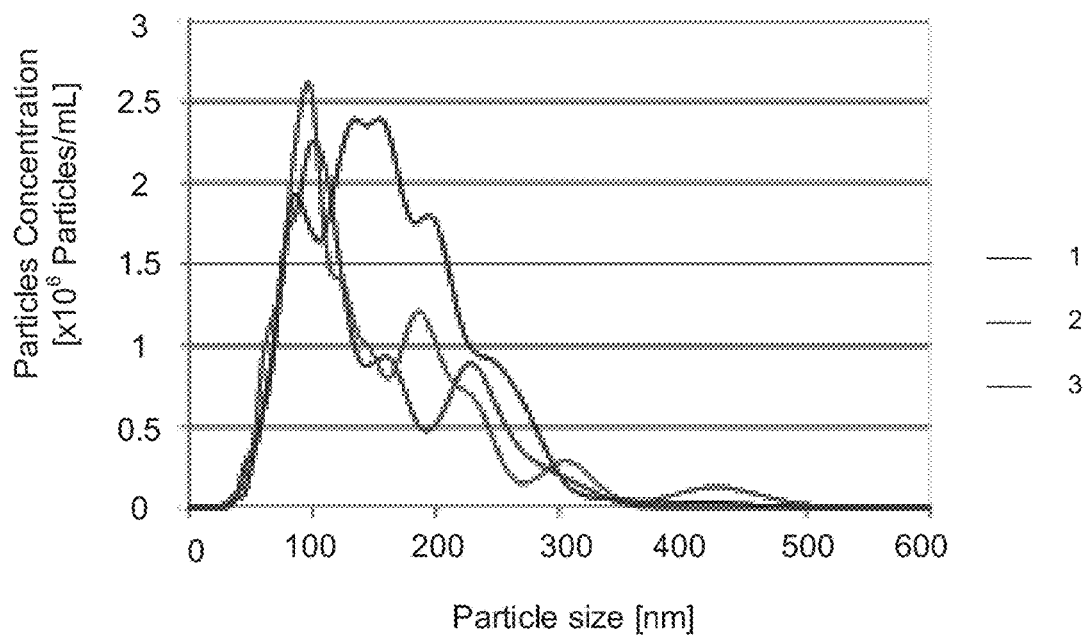
FIG. 3B, FIG. 3C, FIG. 3D and FIG. 3E are graphs showing EV particle sizes as a function of polypeptide precursor concentration at a concentrations of 0 μM (control), 5 μM, 50 μM and 500 μM, respectively.
Figure 3C:
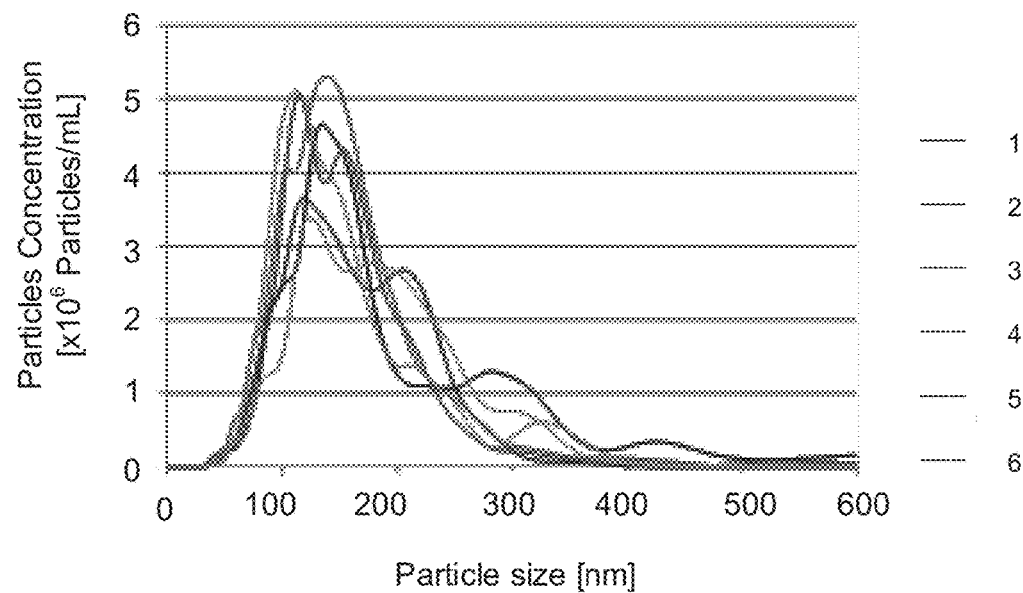
Figure 3D:
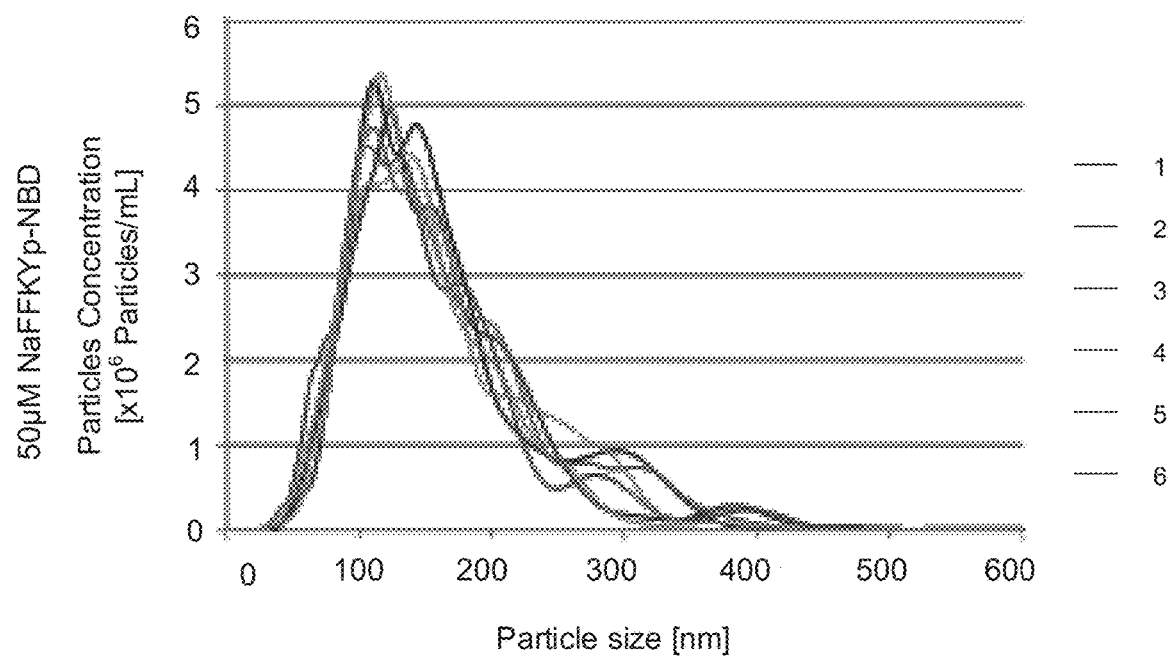
Figure 3E:
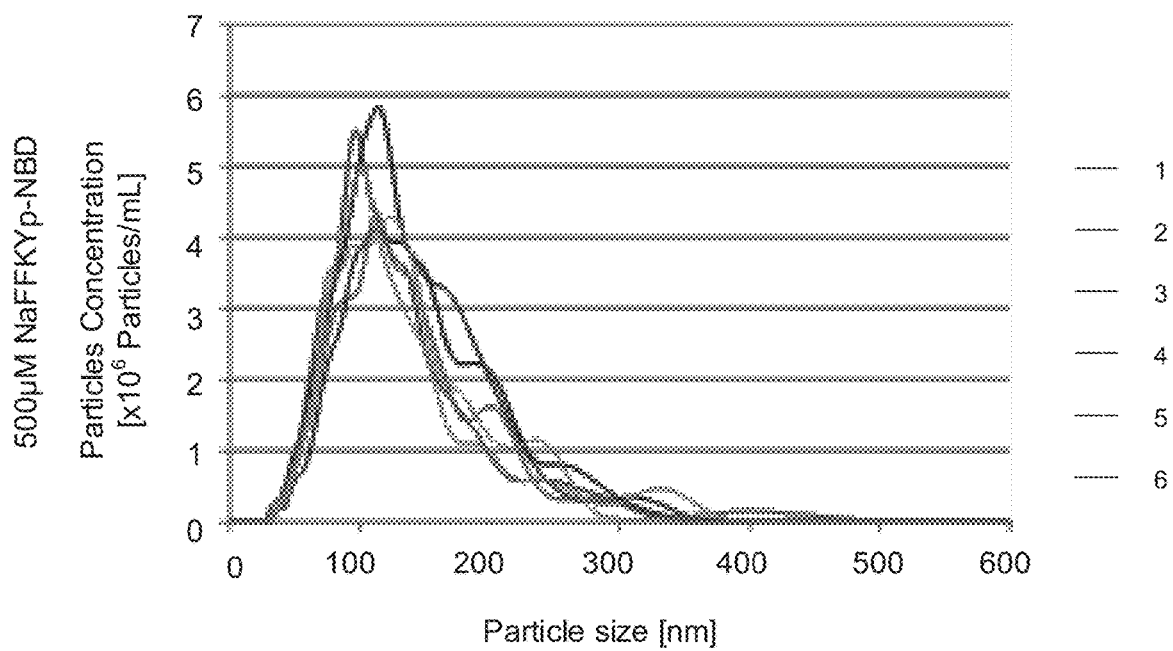

FIG. 3A is a graph showing the number of exosomes released from MDA-MB231 breast cancer cells where the peptide is polymerized before exosome release is determined by Nanoparticle Tracking Analysis (NTA) (NanoSight NS500, Malvern Co.). As the concentration of polymer increases, the number of released exosomes is increased. As shown in FIG. 3B, FIG. 3C, FIG. 3D, FIG. 3E the size of released exosomes from the polymer-MB231 cells is determined by NTA. The exosome size is independent of the polymer concentration. Multiple traces of independent trials overlap in each figure, indicating that the size of released exosomes is highly monodisperse. FIG. 3B depicts three trials. FIG. 3C to 3E depict six trials.

FIG. 3A shows that the number of EVs released from the cells is increased as the concentration of peptides in parental cells is increased, where the number of EVs is quantified by Nanoparticle Tracking Analysis (NTA) (NanoSight NS500, Malvern Co.). The NTA can also determine the average diameter of released EVs. While the increase of polymer concentration in parental cells increases the number of released EVs, the size of EVs is constant regardless of the polypeptide concentration in parental cells (FIG. 3B, FIG. 3C, FIG. 3D, FIG. 3E). The increased number of released EVs can also be confirmed by the increase of fluorescence intensity of collected EVs (FIG. 3F), measured by fluorescence spectrometer. The enhanced production (FIG. 3C, FIG. 3D, FIG. 3E) shows a significant enhancement relative to the control (FIG. 3B). In one embodiment, production is enhanced by at least 50% relative to the control. These data serve as the key evidence for the claim to control the number of EVs released from target cells that contains the polypeptides, and further increase of concentration can generate more EVs in 1-3 orders of magnitudes of production enhancement for practical applications. The particular cells used experienced cell death at concentrations above 500 μM of NapFFKYp-NBD. Alternative upper limits may be possible for other cell line and other polypeptide precursors.

Figure 3F:
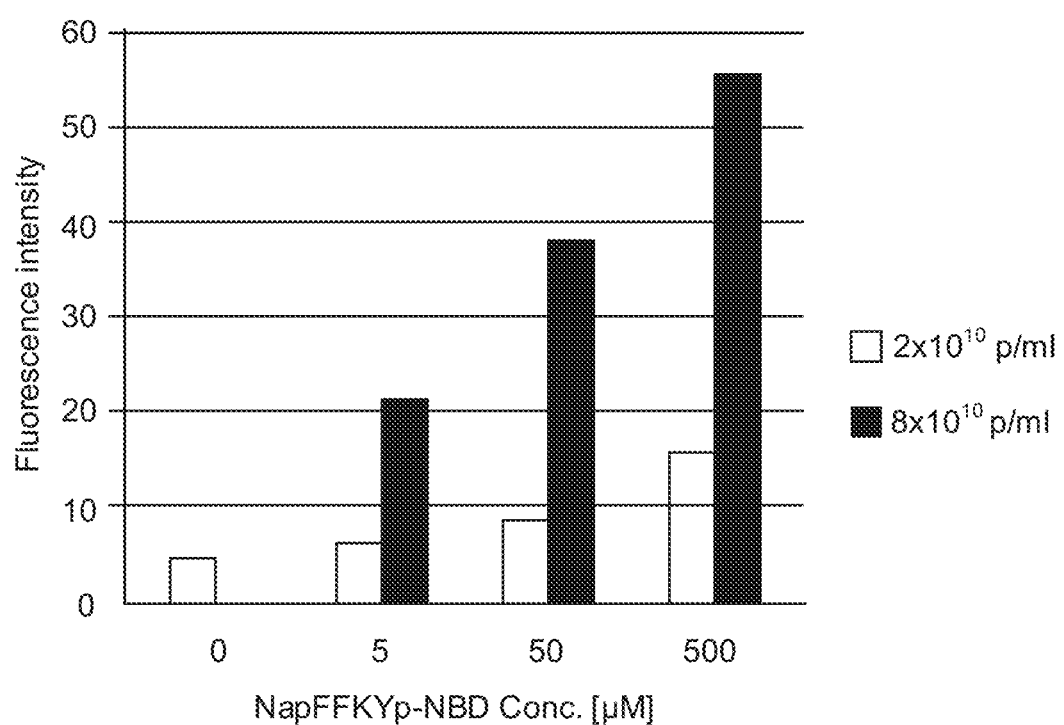
FIG. 3F is a graph depicting fluorescence intensity as a function of increasing polypeptide precursor concentration.

FIG. 3F is a graph depicting florescence intensity of polymerized NapFFK(NBD)Yp inside the exosome in two different concentrations of exosome solutions. The trend (i.e., more precursor incubation induces more polymer in the exosome) is consistent in two exosome solutions.

Figure 4A:
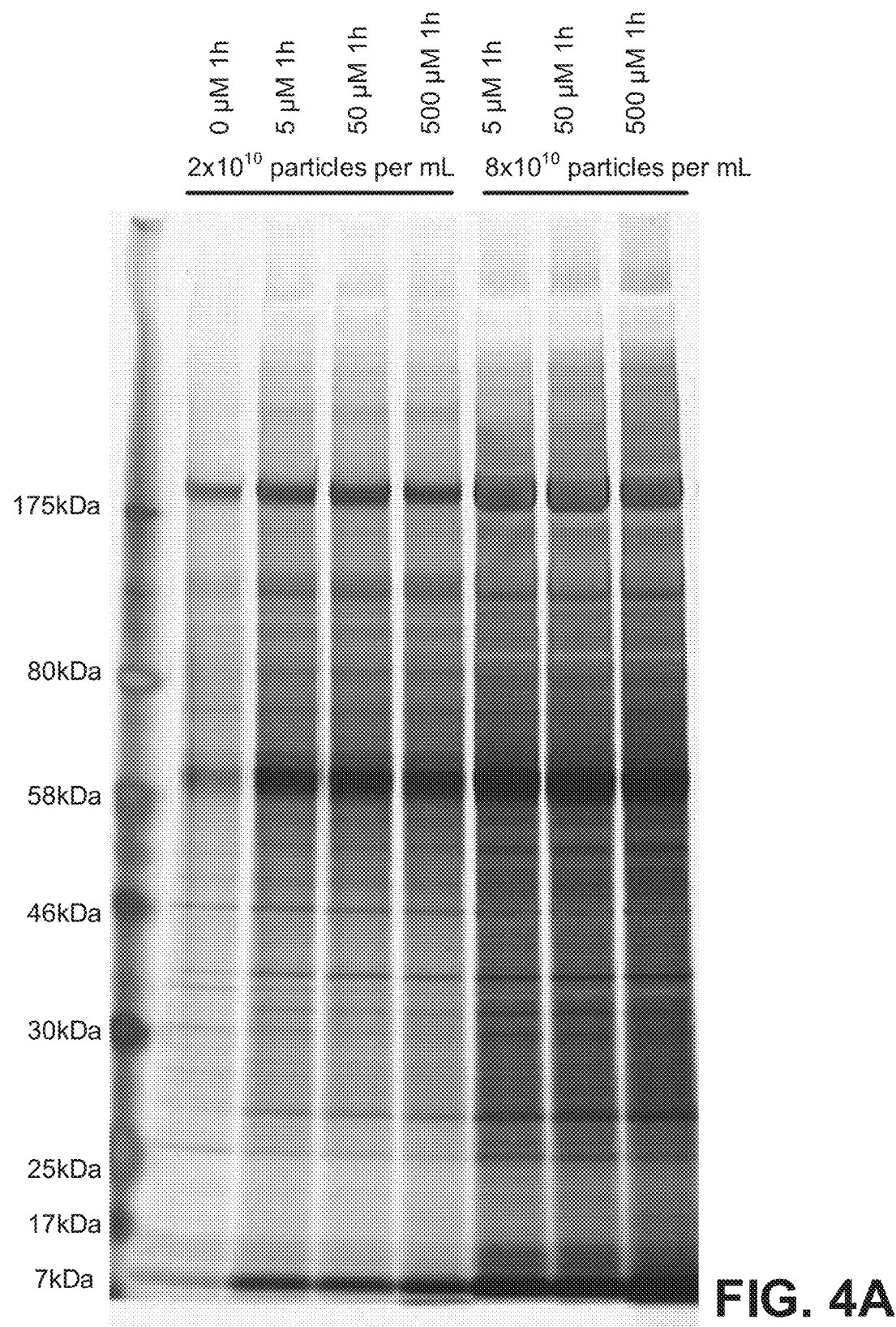
FIG. 4A is an image of a gel showing the total amount of proteins released from cells through EVs carriers increased consistently with the peptide concentration.
Figure 4B:
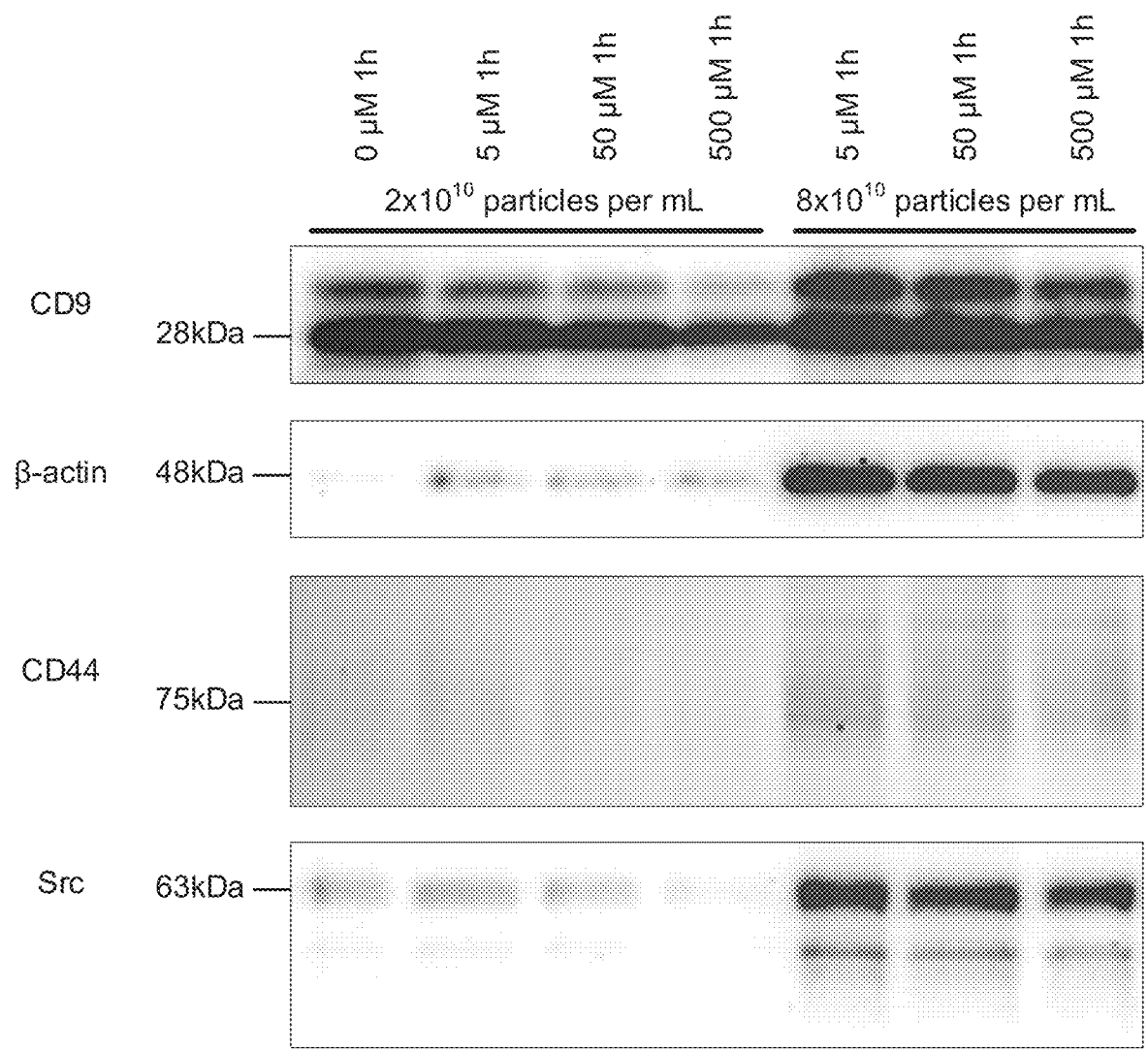
FIG. 4B is an image of a gel showing proteins CD9, CD44, Src, and β-actin, (known as EV markers) show a significant increase from the cells.

There are other evidences of the increased production of EVs by this protocol. When total amount of proteins released from cells through EVs carriers is quantified, these proteins are amount is increased consistently with the peptide concentration (FIG. 4A). The increase of these proteins is proportional to the production of EVs from polypeptide-containing cells, this result supports the amplified generation of EVs via the polypeptide formation. Notably, among these proteins, CD9, CD44, Src, and β-actin, known as EV markers, show the significant increase from the cells (FIG. 4B). In this Western-Blotting, After the simple is transferred by iBlot Gel Transfer Stacks Nitrocelulose (life technologies, IB301002) the following antibodies are used for labeling each protein: (1) anti-CD9 [Clone: 12A12] (Cosmobio, SHI-EXO-MO1, 1:5000) (2) anti-β-actin (SIGMA, A1978, 1:10000) (3) anti-CD44 (SIGMA, HPA005785, 1:1000) (4) anti-Src [36D10] (CST, 2109, 1:1000) (5) anti-mouse IgG-HRP (Bio Rad, 170-6516, 1: 2000). For the secondary antibody, anti-rabbit IgG-HRP (Bio Rad, 170-6515, 1:2000) is applied as a fluorephore.

The consistency of these protein profiles between parental cells and EVs indicates that, even after polypeptides are incorporated in parental cells, these cells and released EVs do not undergo major structural changes.

Previously, various stresses to cells were observed to induce the enhanced production of EVs. The peptide polymerization could also stress cells to induce the enhancement of EV prosecution. However, the disclosed method performs this function in a novel mechanism. Because the peptide polymers are formed around cytoskeletons due to the location of ALP enzyme in cells, these peptide polymers interfere with actin networks and redirect signal pathways to force cells to produce more EVs, a totally new concept for the EV mass-production strategy. For example, when MB231 breast cancer cells were treated with 2.0 ml of 50 μM of the peptide, NapFFK(NBD)Yp, and incubated at a temperature of 10° C. for one hour, this peptide entered cells and ALP around cytoskeleton polymerized the peptide. The samples were centrifuged at 500 rpm for 10 minutes at 10° C. to form a pellet of cells, then the conditioned media in 1 was centrifuged at 3000 rpm for 10 minutes at 10° C. to form another pellet of cells, and then the supernatant was ultracentrifuged at 12.000×g for 20 minutes at 10° C. to form a pellet debris. Finally, after the supernatant fraction of 3 at 100.000×g was ultracentrifuged for 70 minutes at 10° C., exosomes were contained in a pellet. To further refine the exosomes, the pellet was re-suspended in 15.0 ml PBS buffer in the tube, and ultracentrifuged again at 100.000×g for 70 minutes at 10° C.

This peptide polymerization method can also be applied to tag EVs with fluorophores in different ways than could previously be accomplished. Most EVs are tagged by fluorescence dyes that conjugate antibodies and these dyes bind antigen markers displayed on the membrane of target EVs. This traditional approach may not be suitable to image the location of EVs in a long-term body circulation because these markers attached outside EVs could fall off during the circulation. The disclosed method tags EVs by directly incorporating peptides that fluoresce after the peptides are polymerized inside the cells and shedding EVs also contain these fluorescent polymers. When EVs are labeled by dyes inside based on the disclosed method, the tags are more stable as compared to the conventional fluorophore-conjugation outside the EVs. Thus, the disclosed method enables stable labeling of exosomes that can even last for long body circulation.

Most EVs are tagged by dyes that conjugate antibodies and these dyes bind antigen markers displayed on the membrane of target EVs. This traditional approach may not be suitable to image the location of EVs in a long-term body circulation because these markers attached outside EVs could fall off during the circulation. The disclosed method can tag EVs inside the vesicles by directly introducing peptides that fluorescent as peptides are polymerized inside the cells.

When EVs are labeled by dyes inside using this protocol, the tags are more stable as compared to the fluorophore-conjugation outside the EVs. Thus, the disclosed method enables stable labeling of EVs that can even last for long body circulation.

Permeability agents were not necessary to induce the uptake of the peptide to cells. However, to introduce the peptide inside EVs directly, permeabilizing the membrane of EVs with a permeability-enhancing agent is helpful. Relatively mild detergents of saponin and Sodium dodecyl sulfate (SDS) could also be used as alternative permeability-enhancing agents. After the peptide of NapFFK(NBD)Yp penetrates the membrane of EVs, these EVs are held for a few hours for the recovery of membrane structure if necessary. The incorporated peptide is then polymerized inside the EVs as the EV contains the enzyme phosphatase. The brightness of EVs is expected to be proportional to the amount of this peptide inside.

FIG. 4A shows silver staining of proteins in released EVs. After the original EV solution is diluted to $2^{110}$ particles/mL and $8^{10}$ particles/mL by PBS buffer. 15 µL of each simple is mixed with 5 µL of 4×SDS Sample Buffer and treated by heat at 90° C. for 10 min. Then, this sample is run by SDS-PAGE and proteins are silver-stained by Sil-Best Stain One (nacalai tesque, 06865). FIG. 4B shows the sample prepared in (FIG. 4A) (before silver-staining) is also used to examine Western Blotting. The appearance of dark contrast for each protein in higher peptide concentrations indicate that more proteins are detected from increased amount EVs.

Figure 5A:
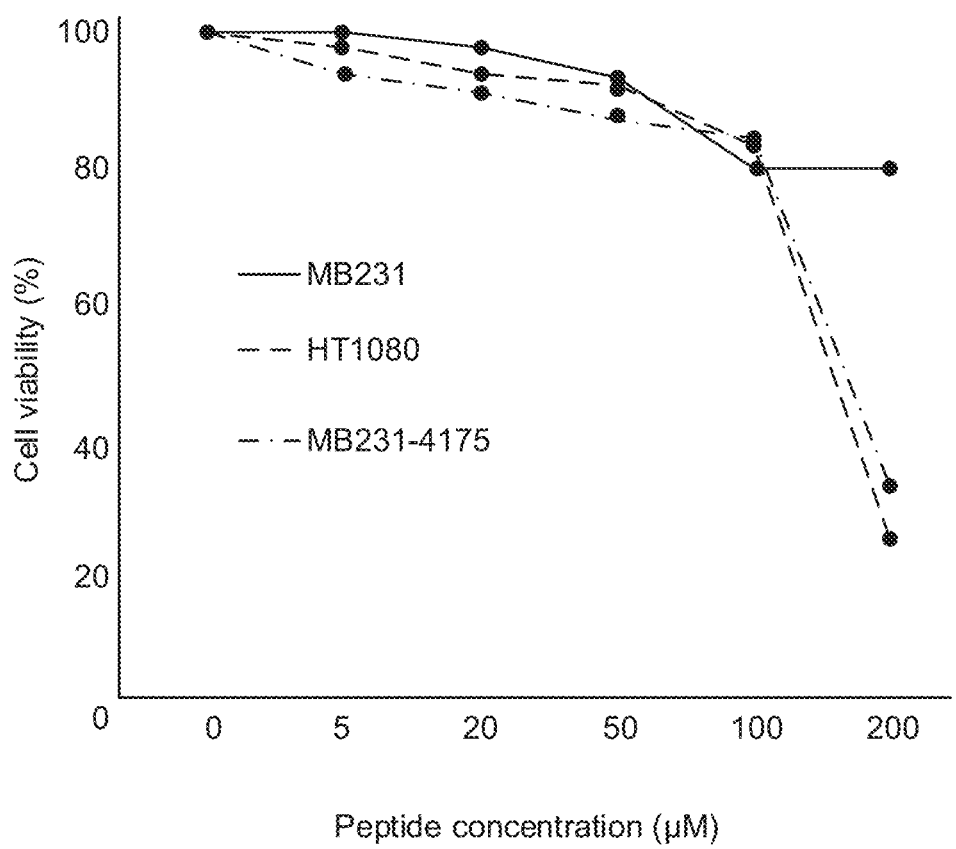
FIG. 5A shows the result of cell tests for various cell types (MB231, HT1080, MB231-4175) in various concentrations of peptide (0-200 μM) after 60 min of incubation.

Unexpectedly, peptides proved to be toxic to cells at higher concentrations. As shown in FIG. 5A toxicity depends on the cell type, however in general cells are viable under 100 µM of peptide incubation (NapFFK(NBD)Yp). Therefore, EV production will be amplified in most of cell types if the peptide concentration does not exceed 100 µM as cell death tends to stop generating EVs. In addition, FIG. 3A showed that EV generation showed significant increase after 60 min incubation in the concentration of 5 µM. Thus, EV generation can be amplified as low as 5 µM of peptide incubation and shorter times to be effective.

Figure 5B:
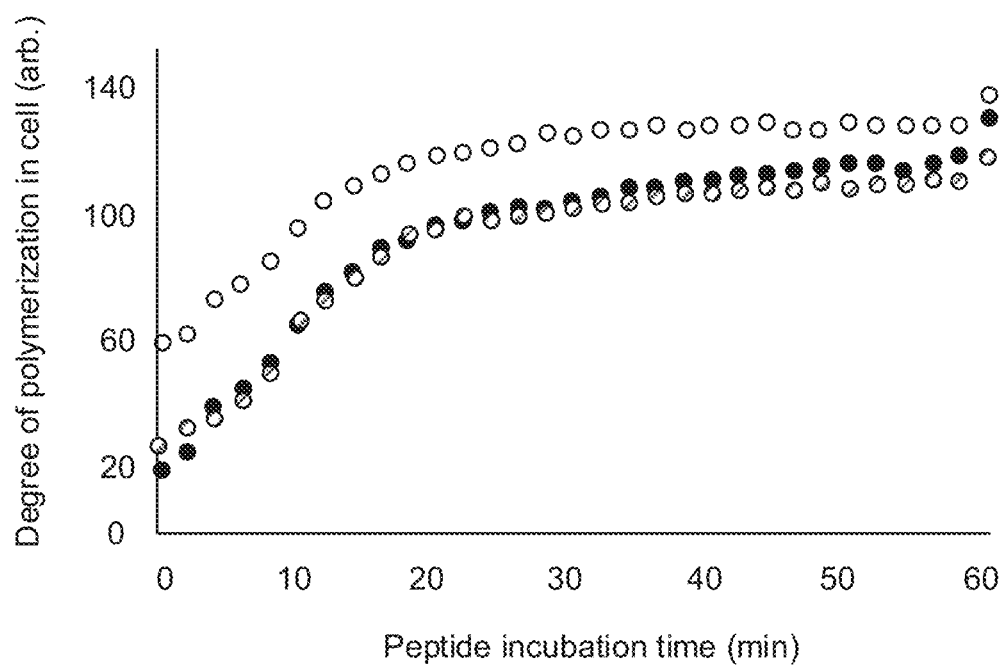
FIG. 5B depicts a graph showing degree of polymerization in H1650 cells with time based on fluorescence change of peptide monomer when the peptide was incubated in the concentration of 200 μM (N=3)

Referring to FIG. 5B, all EV amplification data showed in this figure were obtained with the peptide incubation in 60 min. Thus, this shorter incubation time has significant effect to amplify EV generation. In addition, as shown below, peptide polymerization in H1650 cell (200 µM) reached the highest capacity between 30 and 60 min (N=3). EV generation is typically amplified as the polymerization growth increases in cells, and thus this result indicates that peptide incubation in cells as short as 30 min is the adequate for the EV amplification. In one embodiment, the polymerization is permitted to continue for between 20 minutes and 60 minutes.

Figure 6A:
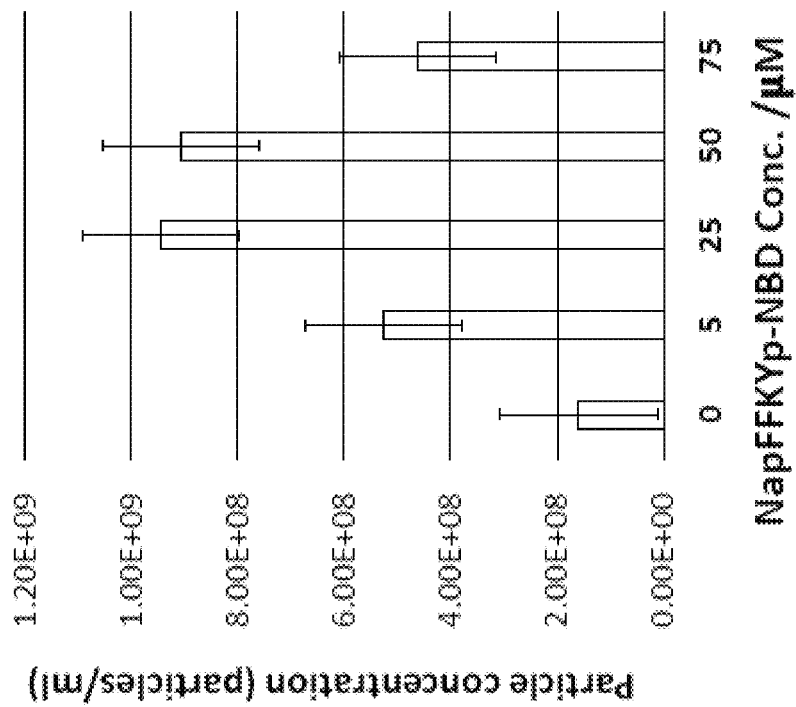
FIG. 6A and FIG. 6B are graphs showing EV concentration released from MB231 cells as a function of peptide concentration incubated in these cells.
Figure 6B:
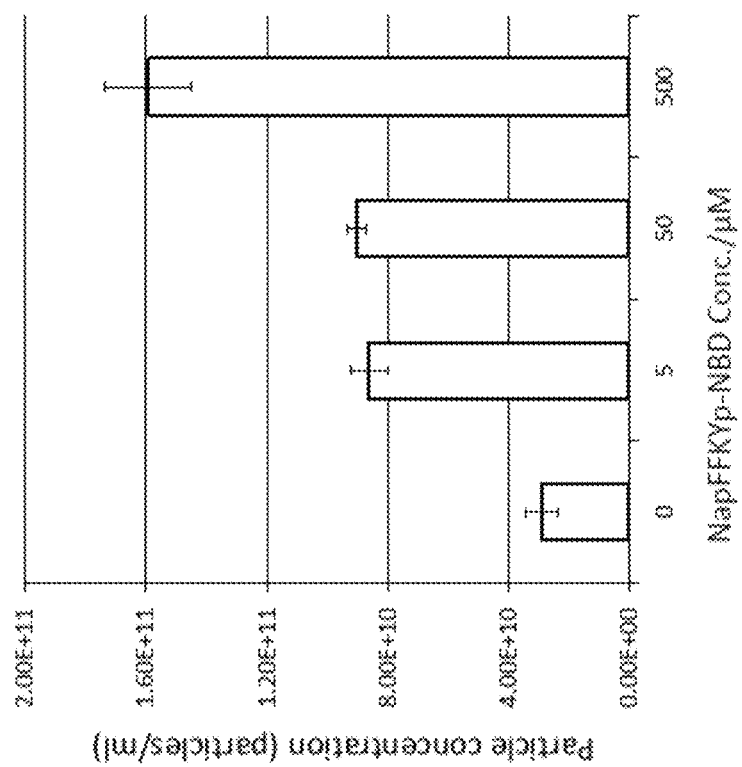

FIG. 6A is a graph of EV concentration that was produced from cells as a function of incubated concentration of NapFFK(NBD)Yp, whose purity was 75.6%. FIG. 6B is also a graph of EV concentration but the peptide was more rigorously purified to 99.9% purify, determined by reversed-phase HPLC and mass spectrometry. Membrane-penetrating agents were not necessary to induce efficient cellular uptake of this peptide. The polymerization of this purified peptide showed an improved performance: a 6-fold increase of EV generation with respect to the control (EVs released from cells that were not treated by the peptide (i.e., 0 µM peptide)) at the peptide concentration of 25 µM, revealing the most amplified EV generation (FIG. 6B). In contrast, the less purified peptide showed only a 3-fold increase of EV generation at <50 µM. In one embodiment, the purified peptide is used as a concentration of between 5 µM but less than 50 µM. In another embodiment, the concentration is between 20 µM and 40 µM. In yet another embodiment, the concentration is between 20 µM and 30 µM. In another embodiment, the concentration is 25 µM.

The disclosed method enables control the number of released EVs by the concentration of polypeptides in parental cells. The method is universal to any cells that contain enzyme phosphatase for the enhancement of EV release. It should be noted that most of cells contain a family of phosphatase so that the method could be very broad for the EV production.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

SEQUENCE LISTING

<110> Research Foundation of the City University of New York
<120> METHOD FOR ENHANCING EXTRACELLULAR VESICLE PRODUCTION
<130> 03284.0108US04
<150> 15/430,821
<151> 2017-02-23
<150> 16/436,221
<151> 2017-02-13
<150> 62/293,852
<151> 2016-02-11
<160> 3
<170> PatentIn version 3.5
<210> 1
<211> 9
<212> PRT
<213> Artificial Sequence
<220>
<223> Synthetic peptide monomer
<400> 1
Phe Phe Phe Phe Cys Gly Leu Asp Asp
1               5
<210> 2
<211> 12
<212> PRT
<213> Artificial Sequence
<220>

<223> Synthetic monomer peptide
<400> 2
Gly Gly Gly His Gly Pro Leu Gly Leu Ala Arg Lys
1               5                   10
<210> 3
<211> 4
<212> PRT
<213> Artificial Sequence
<220>
<223> Synthetic monomer peptide.
<400> 3
Phe Glu Phe Lys
1

SEQUENCE LISTING

<160> NUMBER OF SEQ ID NOS: 3

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide monomer

<400> SEQUENCE: 1

Phe Phe Phe Phe Cys Gly Leu Asp Asp
1               5

<210> SEQ ID NO 2
<211> LENGTH: 12
<212> TYPE: PRT
<213> ORGANISM: Artificial Sequence
<220> FEATURE:
<223> OTHER INFORMATION: Synthetic monomer peptide

<400> SEQUENCE: 2

Gly Gly Gly His Gly Pro Leu Gly Leu Ala Arg Lys
1               5                   10

<210> SEQ ID NO 3
<211> LENGTH: 4
<212> TYPE: PRT
<213> ORGANISM: Artificial Sequence
<220> FEATURE:
<223> OTHER INFORMATION: Synthetic monomer peptide.

<400> SEQUENCE: 3

Phe Glu Phe Lys
1

What is claimed is:

1. A method of enhanced extracellular vesicle production, the method comprising sequential steps of:
   treating the plurality of cells with NapFFK(NDB)Yp at a concentration of at least 5 µM and less than 40 µM, wherein the NapFFK(NDB)Yp had been purified to a purity of at least 93%;
   permitting the NapFFK(NDB)Yp to polymerize within cells in the plurality of cells due to an enzyme within the cells to form a modified cell culture; and
   isolating a first quantity of extracellular vesicles from the modified cell culture, wherein the first quantity of extracellular vesicles is greater than a second quantity of extracellular vesicles isolated from a corresponding plurality of cells that was not treated with the NapFFK(NDB)Yp.

2. The method as recited in claim 1, wherein the concentration of the NapFFK(NDB)Yp is between 20 µM and 40 µM.

3. The method as recited in claim 1, wherein the concentration of the NapFFK(NDB)Yp is between 20 µM and 30 µM.

4. The method as recited in claim 1, wherein the concentration of the NapFFK(NDB)Yp is 25 µM.

5. The method as recited in claim 1, wherein the enzyme is a phosphatase enzyme.

6. The method as recited in claim 1, wherein the first quantity of extracellular vesicles is at least 6-fold increase as compared with the second quantity.

7. A method of enhanced extracellular vesicle production, the method comprising sequential steps of:
   treating the plurality of cells with NapFFK(NDB)Yp at a concentration of at least 5 µM and less than 40 µM, wherein the NapFFK(NDB)Yp had been purified to a purity of at least 93%;
   permitting the NapFFK(NDB)Yp to polymerize within cells in the plurality of cells due to a phosphatase enzyme within the cells to form a modified cell culture; and
   isolating a first quantity of extracellular vesicles from the modified cell culture, wherein the first quantity of extracellular vesicles is greater than a second quantity of extracellular vesicles isolated from a corresponding plurality of cells that was not treated with the NapFFK(NDB)Yp;

wherein the step of isolating occurs immediately after the step of permitting.

8. The method as recited in claim 1, wherein the step of permitting lasts for between 20 minutes and 60 minutes.

9. The method as recited in claim 7, wherein the step of permitting lasts for between 20 minutes and 60 minutes.

\* \* \* \* \*